US007554341B2

(12) United States Patent
Eisele

(10) Patent No.: US 7,554,341 B2
(45) Date of Patent: Jun. 30, 2009

(54) METHOD AND MEASUREMENT APPARATUS FOR DETERMINING THE TRANSITION IMPEDANCE BETWEEN TWO PARTS OF A SUBDIVIDED NEUTRAL ELECTRODE

(75) Inventor: Florian Eisele, Tübingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 0 days.

(21) Appl. No.: 12/219,215

(22) Filed: Jul. 17, 2008

(65) Prior Publication Data

US 2008/0278179 A1   Nov. 13, 2008

Related U.S. Application Data

(62) Division of application No. 11/569,472, filed as application No. PCT/EP2005/005512 on May 20, 2005, now Pat. No. 7,425,835.

(30) Foreign Application Priority Data

May 25, 2004   (DE) .................... 10 2004 025 613

(51) Int. Cl.
*G01R 27/26* (2006.01)
*A61B 18/04* (2006.01)
(52) U.S. Cl. ........................ 324/682; 606/35
(58) Field of Classification Search ............... 324/633, 324/629, 600, 682, 681, 658, 649, 652, 653, 324/655, 668, 675, 708, 76.51; 606/32, 34, 606/35, 41, 42; 702/107, 124; 331/183
See application file for complete search history.

(56) References Cited

U.S. PATENT DOCUMENTS

| | | | |
|---|---|---|---|
| 3,913,583 A | 10/1975 | Bross | |
| 3,933,157 A | 1/1976 | Bjurwill et al. | |
| 4,200,104 A | 4/1980 | Harris | |
| 4,416,276 A | 11/1983 | Newton et al. | |
| 4,818,954 A | 4/1989 | Flachenecker et al. | |
| 5,087,257 A | 2/1992 | Farin et al. | |
| 5,150,683 A * | 9/1992 | Depa et al. | 123/406.45 |
| 5,231,359 A * | 7/1993 | Masuda et al. | 324/675 |
| 5,267,997 A | 12/1993 | Farin et al. | |
| 5,688,269 A | 11/1997 | Newton et al. | |
| 6,205,857 B1 | 3/2001 | Nakajima | |

(Continued)

FOREIGN PATENT DOCUMENTS

DE   1 139 927   11/1962

(Continued)

*Primary Examiner*—Vincent Q Nguyen
*Assistant Examiner*—Hoai-An D Nguyen
(74) *Attorney, Agent, or Firm*—Dickstein Shapiro LLP

(57) ABSTRACT

A method and a measurement apparatus are provided for determining the transition impedance between two electrode parts of a subdivided neutral electrode used in high-frequency surgery. These makes it possible for the purely capacitive component of the transition impedance to be measured. For this purpose a resonant-frequency shift is measured, which occurs when a basic resonant circuit is expanded to an expanded resonant circuit by incorporating the two electrode parts into it in parallel. In particular, in order to determine the basic resonant frequency of the basic resonant circuit and/or the sample resonant frequency of the expanded resonant circuit, the phase shift between current and voltage is measured and the frequency is adjusted until current and voltage are in phase.

9 Claims, 1 Drawing Sheet

U.S. PATENT DOCUMENTS

| | | |
|---|---|---|
| 6,275,786 B1 | 8/2001 | Daners |
| 6,437,582 B1 | 8/2002 | Rode et al. |
| 6,860,881 B2 | 3/2005 | Sturm et al. |
| 7,086,593 B2 * | 8/2006 | Woodard et al. ............ 235/449 |
| 7,300,435 B2 | 11/2007 | Wham et al. |
| 2008/0139087 A1 * | 6/2008 | Togawa et al. ................. 451/8 |

FOREIGN PATENT DOCUMENTS

| | | |
|---|---|---|
| DE | 197 14972 | 10/1998 |
| WO | WO 96/19152 | 6/1996 |
| WO | WO 2004/028385 | 4/2004 |

* cited by examiner

METHOD AND MEASUREMENT APPARATUS FOR DETERMINING THE TRANSITION IMPEDANCE BETWEEN TWO PARTS OF A SUBDIVIDED NEUTRAL ELECTRODE

CROSS REFERENCE TO RELATED APPLICATIONS

The present application is a divisional of U.S. application Ser. No. 11/569,472, filed on Nov. 21, 2006 now U.S. Pat. No. 7,425,835, is a section 371 of International Application No. PCT/EP2005/005512 filed on May 20, 2005, which was published in the German language on Dec. 8, 2005, under International Publication No. WO 2005/115262 A1 and the disclosures of all of which are incorporated herein by reference in their entirety.

BACKGROUND OF THE INVENTION

The present invention relates to a method of determining the transition impedance between two parts of a subdivided neutral electrode used in high-frequency surgery. In addition, a measurement apparatus for determining the transition impedance between two parts of a subdivided neutral electrode used in high-frequency surgery is described, which comprises a resonant circuit into which the two electrode parts can be incorporated in parallel as well as a current-supply device by means of which an alternating measurement voltage can be impressed into the resonant circuit.

In high-frequency surgery high-frequency electrical energy is supplied to the tissue to be treated. A distinction is generally made between a monopolar and a bipolar mode of employing the high-frequency current.

For monopolar use only one active electrode is provided, to which a high-frequency alternating voltage is supplied. Furthermore, it is necessary to apply a neutral electrode to a large area of the patient's body, by means of which the circuit is closed owing to current flow through tissue between the active and neutral electrodes. The shape of the active electrode depends on the particular purpose for which it is employed. The surface area of the active electrode by way of which alternating current is conducted into the tissue is relatively small, so that in the immediate surroundings of the active electrode there is a high current density and hence also a large amount of heat is developed.

The current density decreases rapidly at progressively greater distances from the active electrode, insofar as considerable differences in tissue conductivity do not increase the current density at other places in the body. The alternating currents supplied to the active electrode are conducted away through the neutral electrode. Accordingly, care should be taken to place the neutral electrode in contact with the patient's body over a large area, so that it presents only a slight transition resistance to the high-frequency alternating current.

For bipolar use two active electrodes are provided, between which the tissue to be treated is enclosed. The electrical circuit is closed by the tissue lying between the two active electrodes, which thus becomes heated when a high-frequency alternating voltage is applied. During this process the major proportion of the current flows between the two active electrodes, but in case of aberration there may be some current flow in neighboring parts of the patient's body. In order to conduct such diverted currents away from the body over a large area, so that they do not cause any undesired burns, even when bipolar instruments are used in some cases a neutral electrode is employed, which again should be placed in contact with the patient's body over a large area. The neutral electrode prevents an elevated current density in parts of the body other than that between the active electrodes, and avoids undesired burns.

If part of the neutral electrode should become separated from the tissue, so that the current flow is restricted to those parts of the neutral electrode that remain in contact, higher current densities and hence burning of the tissue can result. As is shown by the following references to the state of the art, various monitoring systems are known by means of which the transition resistance of the neutral electrode can be evaluated.

A high-frequency surgical appliance with a neutral electrode divided into two parts and circuitry for measuring the resistance between the two parts of the neutral electrode is described in the document DE-AS 1 139 927. In this appliance there is provided an accessory direct-current circuit with a source of direct current, to which the two electrode parts are connected in series, so that the only connection between the two electrode parts consists of the patient's body. If the ohmic resistance measured between the two electrode parts exceeds a certain limiting value, the high-frequency generator of the surgical appliance is switched off and/or an alarm system is triggered.

A control circuit for controlling the output of a high-frequency generator in dependence on the measured high-frequency current flowing between an active electrode and a neutral electrode is known from U.S. Pat. No. 3,913,583. The high-frequency current intensity depends on the apparent resistance between active electrode and neutral electrode, so that the output of the high-frequency generator is ultimately regulated in dependence on the apparent resistance.

Furthermore, from U.S. Pat. No. 3,933,157, U.S. Pat. No. 5,087,257 and WO 9619152 neutral-electrode monitoring systems are known by means of which the apposition of a two-part neutral electrode to a patient is evaluated by measuring the apparent resistance between the two parts of the neutral electrode. For this purpose a measurement circuit is provided into which the two electrode parts are incorporated in such a way that the measurement circuit is closed by way of the part of the patient's tissue that is situated between the two electrode parts. To determine the apparent resistance, an alternating voltage is applied to the measurement circuit.

From U.S. Pat. No. 4,200,104 a monitoring system for a two-part neutral electrode is known that is intended to detect a separation of part of the neutral electrode from the patient by measuring the capacitance between the two parts of the neutral electrode. The proposed circuitry for capacitance measurement comprises a monostable multivibrator to the input of which is delivered a signal at constant frequency. The two electrode parts of the neutral electrode are incorporated into the multivibrator circuitry in such a way that the capacitance between these two electrode parts influences the pulse width of the output signal from the monostable multivibrator. The capacitance is to be found by evaluating this pulse width, and this information is then used to draw conclusions about the area over which the neutral electrode is in contact with the patient. However, the pulse width of the multivibrator circuit is also influenced by the ohmic resistance between the two electrode parts, which can also change depending on the contact area of the neutral electrode. Separation of the influences exerted by the capacitance from those exerted by the ohmic resistance seems to be impossible with the circuitry proposed here.

DE 197 14 972 A1 also describes an apparatus for monitoring the application of a bipartite neutral electrode. This apparatus comprises an impedance sensor that detects the transition resistances at the surface of each of the two electrode parts connected in series. The apparatus is galvanically separated from the electrode-part surfaces by means of a transformer. Measurement of the transition resistance at the patient makes use of the fact that this resistance is in each case disposed parallel to the transformer and to a capacitance, and accordingly a parallel oscillating circuit is formed. By triggering the damped oscillating circuit at its resonant frequency, the voltage is determined solely by the transition resistance at the patient. Accordingly, the voltage measured at the resonant frequency allows conclusions to be drawn about the transition resistance at the patient.

The transition between the body of the patient and the neutral electrode opposes the high-frequency alternating current not only by an ohmic resistance, but also by a capacitive resistance determined by charging effects. The above-mentioned monitoring systems in the state of the art are limited to detecting either the ohmic resistance or the apparent resistance in this transition impedance.

The document U.S. Pat. No. 4,200,104 also describes a device for measuring capacitance and thereby estimating the contact area of the neutral electrode, but the capacitance measurement by the measurement device proposed there is influenced by the ohmic component of the transition impedance.

BRIEF SUMMARY OF THE INVENTION

The object of the present invention is to provide a measurement apparatus and a method that make possible an improved evaluation of the extent to which the neutral electrode is in contact with the patient.

According to one aspect of the invention there is provided a method of determining the transition impedance between two electrode parts of a subdivided neutral electrode for use in high-frequency surgery, by providing a resonant circuit into which said two electrode parts are incorporated in parallel with one another such that the is a transition impedance between them; measuring a resonant-frequency shift in said resonant circuit; and determining the purely capacitive component of the transition impedance using said resonant-frequency shift. According to another aspect of the invention there is provided a measurement apparatus for determining the transition impedance between two electrode parts of a subdivided neutral electrode for employment in high-frequency surgery, comprising a resonant circuit within which said two electrode parts are connected in parallel; a current-supply device adapted to impress a measurement alternating voltage into the resonant circuit; a phase-measuring device; and a control means adapted to determine the phase of the current and of the voltage by means of the phase-measuring device in order that the frequency of the current-supply device can be controlled by the control means in such a way that current and voltage are in phase.

In the present invention the fact that the transition impedance is made up of both an ohmic and a capacitive resistance is taken into account. The transition impedance is represented in vector form as the vector sum of a real vector for the ohmic resistance and a complex vector for the capacitive resistance; the value of the transition impedance is here termed "apparent resistance".

Because the capacitive resistance is frequency-dependent, measurement of the apparent resistance at a test frequency does not in itself provide reliable information about the magnitude of the apparent resistance while high frequencies are being employed. For that purpose, it would be necessary to know the relative contribution of the capacitive resistance to the apparent resistance. Accordingly, the invention is based on the provision of a method and a measurement apparatus by means of which the ohmic contribution and the capacitive contribution to the transition impedance can be measured separately. In particular, detection of the purely capacitive part of the transition impedance makes it possible to infer the size of the contact area between the neutral electrode and the patient's body. Furthermore, from the capacitive resistance measured at a test frequency it is possible to calculate the capacitive resistance during high-frequency employment, which provides the surgeon with additional valuable information enabling the current amplitude and frequency to be adjusted to suit the intended high-frequency usage.

To determine the transition impedance it is advantageous to use a subdivided neutral electrode, in particular a neutral electrode divided into two parts in such a way that the two electrode parts are electrically insulated from one another and both are placed in contact with the tissue, in particular the skin, of the patient. The two electrode parts can be incorporated into a measurement circuit so that they are electrically connected only by way of the patient's tissue. The transition impedance between the two electrodes is determined by the two partial impedances at the places where the two electrode parts make contact with the patient's tissue as well as by the conductivity of the tissue situated between the two electrode parts. Accordingly, the transition impedance between the two electrode parts can be regarded in general as a measure of the degree to which the neutral electrode makes contact with the patient's tissue.

A method in accordance with the invention is therefore designed for determining the transition impedance between two electrode parts of a subdivided neutral electrode for use in high-frequency surgery, and is characterized in that with this method the purely capacitive component of the transition impedance is determined.

For determining the capacitive component of the transition impedance a resonant circuit or parallel resonant circuit is employed, in which an inductance is provided in parallel to a capacitance. This makes use of the fact that the resonance condition of the resonant circuit depends on its capacitance and inductance, as well as its ohmic resistance, if present. The resonant frequency changes when the two electrode parts are connected in parallel to the resonant circuit, so that the transition impedance is likewise parallel to the resonant circuit. With the method in accordance with the invention the capacitive portion of the transition impedance is found by measuring the alteration of resonant frequency caused by connecting the two electrodes in parallel to the resonant circuit.

When the purely capacitive component of the transition impedance is to be determined, it is preferable to proceed according to the following steps. For the first measurement a resonant circuit should be made available that is not connected to a transition impedance; this will be termed the basic resonant circuit. It comprises a measurement inductance and a coupling capacitance. The coupling capacitance is preferably provided by the coupling capacitors in general use, one of which is to be disposed in each branch of a branched lead connected to the neutral electrodes, and which together should help to make sure that the current is uniformly distributed between the two electrode parts. The measurement inductance is parallel to the coupling capacitance and serves to complete the resonant circuit. The component used to provide measurement inductance is preferably a coil, the inductance of which is appropriate for adjusting the basic resonant circuit to a suitable resonant frequency. Whereas the coupling capacitors are preferably disposed in the basic resonant circuit and in the high-frequency circuit, the measurement inductance is preferably disposed only in the basic resonant circuit and not in the high-frequency circuit.

The first measurement thus involves a resonant frequency of the above-mentioned basic resonant circuit, which hereinafter will be termed "basic resonant frequency".

For the second measurement the basic resonant circuit is expanded by adding, in parallel, the transition impedance. In the second measurement the resonant frequency of this expanded resonant circuit is measured; this will hereinafter be termed the "sample resonant frequency".

The procedure for finding the capacitive component of the transition impedance is based on a model according to which the transition impedance can be sufficiently well represented by a purely ohmic resistance positioned within the circuit in parallel to a purely capacitive resistance. This model provides a good approximation to the actual transition impedance. On the basis of this model the capacitive contribution to the transition impedance can be found from the basic resonant frequency, the sample resonant frequency and the measurement inductance.

Preferably for calculation of the capacitive resistance the associated capacitance $C_x$ of the transition between the two electrode parts is calculated from the measured basic resonant frequency $f_1$, the measured sample resonant frequency $f_2$ and the measurement inductance L.

For the resonance condition of the basic resonant circuit the following formula applies:

$$2\pi f_1 C_0 - \frac{1}{2\pi f_1 L} = 0$$

where $C_0$ is the coupling capacitance of the basic resonant circuit.

For the resonance condition of the expanded resonant circuit the following formula applies:

$$2\pi f_2 (C_0 + C_X) - \frac{1}{2\pi f_2 L} = 0$$

The capacitance $C_x$ of the transition between the two electrode parts is found by combining these two resonance conditions with one another:

$$C_X = \frac{1}{4\pi^2 L}\left(\frac{f_1^2 - f_2^2}{f_1^2 f_2^2}\right)$$

The capacitive resistance $X_c$ for a particular frequency f is calculated by the following formula:

$$X_C = \frac{1}{2\pi f C_X}$$

In the resonance case of the basic resonant circuit or the expanded resonant circuit, current and voltage are in phase within an electrical lead supplying the relevant resonant circuit. This phase requirement for the resonance case is preferably imposed for determining the basic resonant frequency and the sample resonant frequency. In particular it is proposed that for measuring the basic resonant frequency of the basic resonant circuit or the sample resonant frequency of the expanded resonant circuit, a measurement alternating voltage is applied to the basic resonant circuit or the expanded resonant circuit, and the phase shift between current and voltage is measured in a lead supplying the corresponding current. The frequency of the measured alternating voltage as adjusted until current and voltage are in phase, and accordingly the associated resonant circuit is in resonance. In this process the frequency can be varied by scanning a specified frequency range, until the resonance condition has been achieved. Preferably, however, a control means is provided that adjusts the frequency of the measurement alternating voltage to the resonant frequency in dependence on the measured phase relations according to a control algorithm, in particular a proportional-integral control algorithm.

Additional advantages are obtained when the measurement alternating voltage is generated by a constant-current source that delivers a square-wave alternating-current signal with constant current amplitude to the basic resonant circuit and/or to the expanded resonant circuit. It is particularly advantageous for the frequency of the alternating-current signal to be adjustable by means of a timer signal that in particular is controlled by a control means, so that the zero crossing and the frequency of the alternating-current signal are already known by way of the timer signal.

Another known feature is that when the basic or the expanded resonant circuit is in the resonance situation, the impedance of the circuit is determined exclusively by the ohmic resistance. In this resonance case, therefore, the voltage across the associated resonant circuit is maximal. This resonance condition can be exploited to measure the basic resonant frequency of the basic resonant circuit or to measure the sample resonant frequency of the expanded resonant circuit. For this purpose a measurement alternating voltage should be applied to the relevant resonant circuit and the voltage across the said circuit is then measured. The frequency of the measurement alternating voltage is adjusted until the voltage reaches a maximal value. Preferably a constant-current source is used as current source.

As has already been discussed above, it is desirable to make available a method and a measurement apparatus that can be used to measure separately the ohmic component and the capacitive component of the transition impedance. Accordingly, the method will preferably also include determination of the ohmic component of the transition impedance. As a result, the transition impedance is also known, as well as the relative contributions of the ohmic resistance and the capacitive resistance to the transition impedance, so that it is possible to make a well-founded assessment of the extent of contact between patient and neutral electrode. In particular, the phase angle of the transition impedance can be calculated on the basis of the ohmic and the capacitive components.

The ohmic resistance is determined by utilizing the fact that in the case of resonance of the basic resonant circuit or the expanded resonant circuit, the transition impedance is given exclusively by the ohmic resistance. If in the resonance case the current in a lead connected to the expanded resonant circuit and the voltage across the expanded resonant circuit are measured, from these values the ohmic resistance of the transition impedance can be calculated directly, insofar as the ohmic resistance of the basic resonant circuit is negligibly small. The ohmic resistance is found by dividing a peak value of the voltage signal by a peak value of the current signal. On the other hand, if the basic resonant circuit exhibits a considerable ohmic resistance, this can be determined analogously in the basic resonant circuit.

Because the electrode parts can become detached even during high-frequency employment, it is recommended that the transition impedance be monitored by measuring the sample resonant frequency of the expanded resonant circuit at certain time intervals. As a rule, this requires a brief interruption of the high-frequency operation.

It is furthermore advantageous for it to be possible to detect which of the two electrode parts is making the worse contact. For this purpose, especially during employment for high-frequency surgery, it is preferable to measure the current flowing away from each of the electrode parts independently.

Regarding the apparatus, the invention relates to a measurement apparatus for determining the transition impedance between the two parts of a subdivided neutral electrode for use in high-frequency surgery. The measurement apparatus comprises a resonant circuit in which the two electrode parts can be arranged in parallel, and a current-supply device by means of which a measurement alternating voltage can be impressed on the resonant circuit.

Thus when the idea underlying the invention is applied to a measurement apparatus, said measurement apparatus is designed to determine the purely capacitive component of the transition impedance. For this purpose there are provided a control means and a phase-measurement device, and the current-supply device, control means and phase-measurement device are designed so that the phase-measurement device signals to the control means the phase of the current and voltage of the measurement alternating current applied to the resonant circuit, and the frequency of the current-supply device can be controlled by the control means in such a way that current and voltage are in phase.

Costs are reduced when the measurement apparatus is operated at the "patient's circuit potential". Then there is no need for a galvanic separation between parts of the measurement apparatus and the "patient's circuit potential", which is ordinarily implemented by expensive transformers. Only a galvanic separation of the current-supply device and other parts of the measurement apparatus from the intermediate circuitry of the high-frequency surgical appliance is required, and this can be implemented for instance by DC/DC converters and optoelectronic couplers. Hence in accordance with the invention the measurement alternating voltage is fed directly from the current-supply device into the resonant circuit.

When the electrode parts are not included in the circuitry, the resonant circuit corresponds to the basic resonant circuit and comprises a coupling capacitance and a measurement inductance parallel thereto. As mentioned above with reference to the method in accordance with the invention, the coupling capacitors, one of which is disposed in each branch of the bifurcated lead connected to the neutral electrode, are used to provide coupling capacitance, whereas the measurement inductance is preferably not disposed within the high-frequency circuit.

Furthermore, it is advantageous for the resonance condition of the resonant circuit to be determinable with reference to the phase relation between current and voltage, in particular within a lead connected to the resonant circuit. For this purpose the current-supply device is preferably a constant-current source, the frequency of which can be set by the control means, by way of a timer signal, and which generates a square-wave alternating current as output.

Accordingly, the zero crossing of the current and the applied frequency can be detected by the control means with reference to the timer signal. Preferably an analog comparator is provided, by way of which the zero crossing in a lead connected to the resonant circuit can be determined by the control means, so that the control means can detect the phase difference between current and voltage by way of the timer signal and the analog comparator.

In particular for determining the ohmic resistance there is preferably provided a voltage-measurement device for measuring the voltage across the resonant circuit, so that a peak value of the voltage can be measured under the resonance condition of the resonant circuit when transition impedance is included in the circuit.

In particular for evaluating which of the two electrode parts is making better contact, at every branch of the lead running to an electrode part of the neutral electrode there is disposed a current sensor by means of which the current flowing away from the associated electrode part can be measured.

Additional advantageous embodiments of the proposed measurement apparatus will to a great extent be evident from the above explanations of the method in accordance with the invention in terms of the essential features of the invention as well as their advantageous embodiments, converted to an implementation in the measurement apparatus according to circuit technology.

The invention further relates to a high-frequency surgical appliance with at least one active electrode and one subdivided neutral electrode that comprises a measurement apparatus in accordance with the invention for determining the transition impedance between two electrode parts of the subdivided neutral electrode.

BRIEF DESCRIPTION OF THE SEVERAL VIEWS OF THE DRAWINGS

The foregoing summary, as well as the following detailed description of the invention, will be better understood when read in conjunction with the appended drawing. For the purpose of illustrating the invention, there is shown in the drawing embodiments which are presently preferred. It should be understood, however, that the invention is not limited to the precise arrangements and instrumentalities shown.

In the drawing.

DETAILED DESCRIPTION OF THE INVENTION

Figure 1:
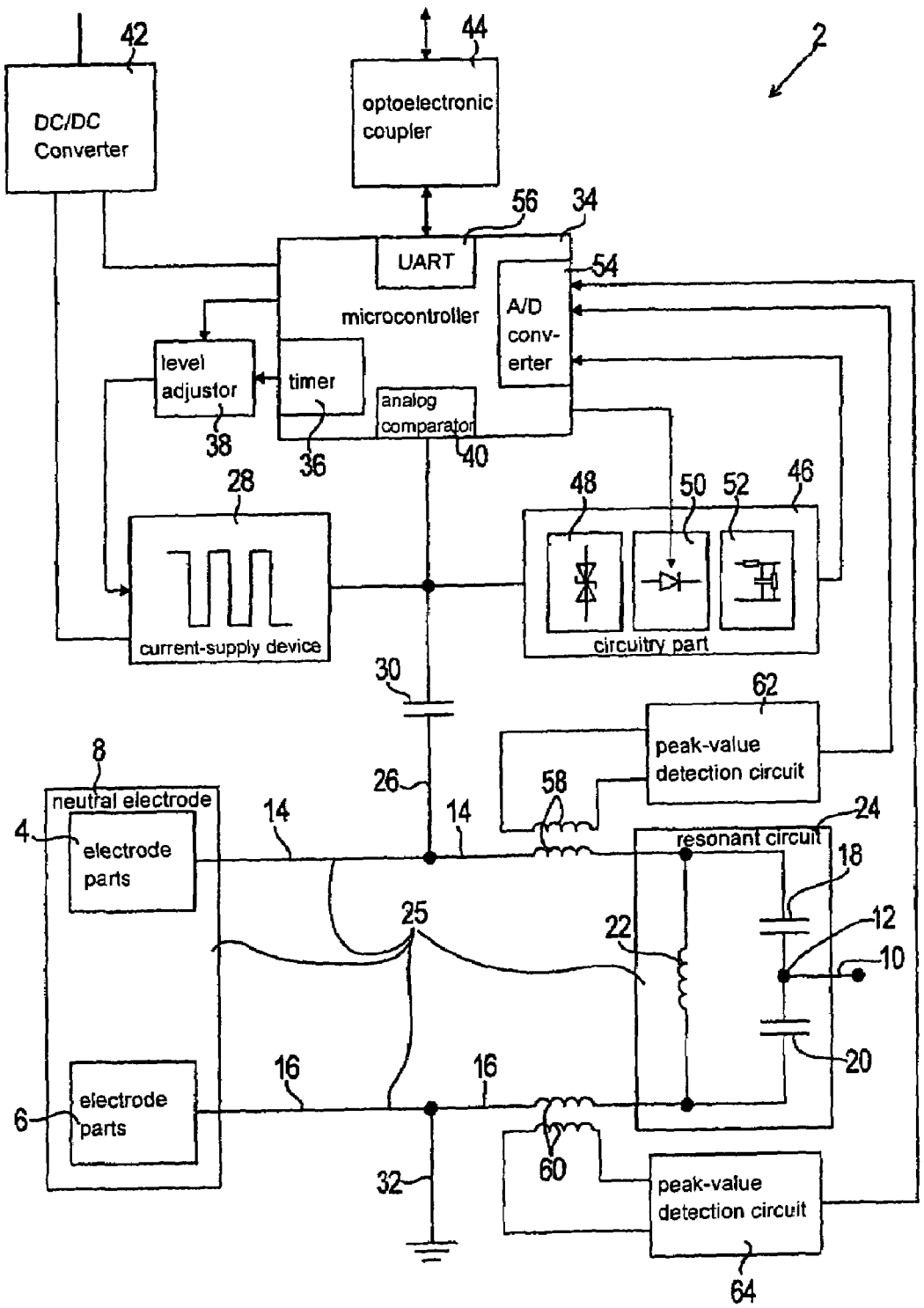
FIG. 1 shows the circuit arrangement of a measurement apparatus in accordance with the invention.

With the measurement apparatus 2 shown here, both the capacitive component and the ohmic component of the transition impedance between two electrode parts 4, 6 of a neutral electrode 8 can be measured. The two electrode parts 4, 6 are electrically insulated from one another, such that when both electrode parts 4 and 6 are placed in contact with the body of a patient, an electrical connection between the two electrode parts 4, 6 is produced by the patient's tissue. As a rule the transition impedance between the two electrode parts 4, 6 is measured while the electrode parts 4, 6 are in contact with the patient. However, it is also possible for a direct transition impedance to be measured by placing the electrode parts 4, 6 in contact with one another, in such a way that the contact surfaces of the two electrode parts 4, 6 are in contact with one another and the electrical connection between them is mediated, for instance, by an intervening layer of gel.

In addition the neutral electrode is provided with an electrical lead 10, which at a branch point 12 is split into two branches 14, 16. Each of the branches 14, 16 runs to one of the electrode parts 4, 6, so that an electrical charge at the electrode parts 4, 6 can be conducted away through the branches 14, 16 and the neutral-electrode lead 10 to the grounded part of a high-frequency surgical appliance, in particular a high-frequency current supply means. In each branch 14, 16 of the neutral-electrode lead 10 a coupling capacitor 18, 20 is disposed, so that the coupling capacitors 18, 20 serve to distribute the current uniformly to the two electrode parts 4, 6.

The electrode parts 4, 6 of the branches 14, 16, together with the coupling capacitors 18, and the neutral-electrode lead 10 thus constitute part of a high-frequency electrical circuit. During high-frequency employment of the equipment, high-frequency alternating currents flow through these components.

The coupling capacitors are combined in parallel with a measurement coil 22 to form a basic resonant circuit 24 of the measurement apparatus 2. The two parallel electrode parts 4, 6 can be incorporated in parallel into the basic resonant circuit 24, so as to expand the basic resonant circuit 24 to form an expanded resonant circuit 25 by introduction of a transition impedance between the two electrode parts 4, 6.

From a current-supply device 28, by way of a first lead 26, a measurement alternating voltage can be impressed directly into the basic resonant circuit 24 or into the expanded resonant circuit 25. A capacitor 30 in the first lead 26 serves as a barrier to direct current. A second lead 32 runs from the basic resonant circuit 24 or the expanded resonant circuit 25 to ground, so that the basic resonant circuit 24 or the expanded resonant circuit 25 is positioned in series between the first lead 26 and the second lead 32.

The measurement apparatus 2 further comprises a control means in the form of a microcontroller 34, which is designed for controlling the frequency of the current-supply device 28, for detecting the zero crossing of current and voltage in the first lead 26, for monitoring the value of the voltage in the lead 26, and for monitoring the partial currents flowing away from the two electrode parts 4, 6.

The current-supply device 28 is a voltage-controlled constant-current source that emits a rectangular current signal, the frequency of which can be adjusted by means of a timer signal. The current-supply device 28 is preferably designed to send out voltages amounting to at most ±10V. For controlling the frequency the microcontroller 34 is provided with a timer 36 that sends a timer signal to the current-supply device 28 in order to control the frequency of the measurement alternating voltage. The measurement apparatus 2 further comprises a level adjustor 38 controlled by the microcontroller 34, which enables various measurement currents and hence various measurement regions to be adjusted. As a result, even the high transition impedance of a neutral electrode 8 that has not been placed in contact with a patient can be measured; in this case the electrical connection between the two electrode parts 4, 6 can be produced, for example, by disposing a gel bridge between the two contact surfaces of the electrode parts 4, 6.

The microcontroller 34, by way of an analog comparator 40, detects the zero crossing of the voltage in a lead 26 supplying the basic resonant circuit 24 or the expanded resonant circuit 25. Accordingly, the microcontroller 34 has access to information regarding the phase relation between current and voltage. The microcontroller 34 is designed so that according to a proportional-integral control algorithm it alters the output frequency of the current-supply device 28, by way of the timer signal, in such a way that the phase difference between current and voltage becomes zero. When current and voltage are in phase with one another, the basic resonant circuit 24 or the expanded resonant circuit 25 is being operated at its particular resonant frequency, i.e. in its basic resonant frequency or in its sample resonant frequency, respectively.

The measurement apparatus 2 is operated at the patient circuit potential. However, with respect to an intermediate circuit of the high-frequency surgery appliance the current-supply device 28 and the microcontroller 34 are galvanically separated. This is achieved by a DC/DC converter 42 and optoelectronic coupler 44.

With the circuitry associated with the measurement apparatus 2 described above, the capacitive component of the transition impedance between the two electrode parts 4, 6 can be measured in accordance with the invention.

While the electrode parts 4, 6 are not in contact with the patient, the magnitude of the impedance between the electrode parts 4, 6 is such that the basic resonant circuit 24 is not influenced by the electrode parts 4, 6. Accordingly, when the electrode parts 4, 6 are not in contact with the patient, the basic resonant frequency of the basic resonant circuit 24, which is derived from the coupling capacitance $C_0$ of the coupling capacitors 18, 20 and the measurement inductance L of the measurement coil 22, can be determined.

For this purpose the microcontroller 34 detects the phase difference between current and voltage in the measurement alternating voltage applied to the basic resonant circuit 24 and according to the proportional-integral control algorithm alters the output frequency of the current-supply device 28 in such a way that the phase difference between current and voltage is zero. By referring to the time signal, therefore, the basic resonant frequency $f_1$ of the basic resonant circuit 24 is known.

When the electrode parts 4, 6 are in contact with the patient, the impedance between them is the transition impedance, which is determined by the measurement device 2.

For this purpose a measurement alternating voltage is applied to the expanded resonant circuit 25, which is formed by the transition impedance between the electrode parts 4, 6, the coupling capacitance $C_0$ of the coupling capacitors 18, 20 and the measurement inductance L of the measurement coil 22. The microcontroller 34 detects the phase difference between current and voltage and, again according to the proportional-integral control algorithm, alters the output frequency of the current-supply device 28 in such a way that the phase difference between current and voltage becomes zero. By reference to the timer signal, the sample resonant frequency of the expanded resonant circuit 25 is known.

The capacitance $C_x$ of the transition between the two electrode parts 4, 6 is calculated according to the following equation:

$$C_X = \frac{1}{4\pi^2 L}\left(\frac{f_1^2 - f_2^2}{f_1^2 f_2^2}\right)$$

where $f_1$ is the basic resonant frequency and $f_2$ is the sample resonant frequency.

The capacitive resistance of the transition for a particular frequency f is found by the following equation:

$$X_C = \frac{1}{2\pi f C_X}$$

The above calculation is based on the assumption that the transition impedance can be described by a parallel circuit consisting of an ohmic resistance $R_x$ and a capacitance $C_x$.

For determining the ohmic component of the transition impedance the measurement apparatus 2 comprises a circuitry part 46 to measure the voltage across the basic resonant circuit 24 and/or the expanded resonant circuit 25. The circuitry part 46 comprises a peak-voltage limiter 48 to suppress high-frequency interference, as well as a peak-value detector consisting of a synchronous rectifier 50 and a low-pass filter 52. The synchronous rectifier 50 is driven by a microcontroller 34 by way of a signal derived from the timer signal. The microcontroller 34 further comprises an analog/digital converter 54 and a UART (universal asynchronous receiver-transmitter) 56, so that the measured signal from the circuitry part 46 is digitized by the A/D converter 54 and by means of the UART 56 is transmitted to a control device (not shown) of the high-frequency surgical appliance.

The ohmic resistance $R_x$ of the transition impedance between the two electrodes is obtained from the following equation:

$$R_X = \frac{U_S}{I_S}$$

where $U_s$ is the peak value of the alternating voltage across the resonant circuit and $I_s$ is the peak value of the current intensity. The peak value of the alternating voltage can be measured by way of the circuitry part 46, whereas the peak value of the current intensity $I_s$ is known from the setting of the current-supply device 28, which is constructed as a constant-current source.

The measurement apparatus 2 shown here is additionally designed to measure the high-frequency current flowing away from each of the electrode parts. These partial currents are detected, in particular during a high-frequency application, by the current sensors 58, 60 disposed in the branches 14, 16 of the neutral-electrode lead 10. The output signal from each of the current sensors 58, 60 is sent to an associated peak-value detection circuit 62, 64, whereupon an output signal from the peak-value detection circuits 62, 64 is sent to the A/D converter 54. Accordingly, the partial currents flowing away over the individual electrode parts 4, 6 can be detected by the microcontroller 34. Furthermore, once the measured values regarding the partial currents have been digitized by the A/D converter 54, the UART 56 makes them available for evaluation, in series, to the control device (not shown) of the high-frequency surgical appliance.

Because the invention provides for monitoring of the symmetry of the high-frequency partial currents that appear in the two branches 14, 15 of the neutral electrode lead 10 during a high-frequency application, loss of contact of one electrode part 4, 6 can be detected. The symmetry can be evaluated by establishing the relationship of the two partial currents. By summation of the partial currents the total HF current flowing through the neutral electrode can be calculated. In the case a monopolar high-frequency application, this total current can assist evaluation of the plausibility of a measured value for the output current of the active electrode, and comparison with the latter can enable conclusions to be drawn about the level of a leakage current.

The invention is not limited to the embodiment shown as an example in FIG. 1. Instead the invention results from an expert overall consideration of the claims, the description, the exemplary embodiment and the variants mentioned below, which are intended to provide a person skilled in the art with indications of additional alternative embodiments.

In particular the sequence in which the basic resonant frequency is measured prior to measurement of the sample resonant frequency is not compulsory. Rather, the sample resonant frequency can also be measured first and the basic resonant frequency thereafter. In this regard it is advantageous for the electrodes to be arranged in parallel by means of a switch so that after the sample resonant frequency has been measured, the electrode parts can be separated from the basic resonant circuit by opening the switch; thus for measurement of the basic resonant frequency there is no need to remove the electrode parts from the tissue. Preferably after the high-frequency application has been terminated, a control measurement of the basic resonant frequency is once again carried out.

Furthermore, a sinusoidal current signal can also be used as output signal from the current-supply device.

The functions described for the microcontroller can also be performed entirely or in part by the control device of the high-frequency surgical appliance. In particular it can be provided that the microcontroller of the measurement apparatus is integrated into the control device of the high-frequency surgical appliance.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim

1. Method of determining the transition impedance between two electrode parts of a subdivided neutral electrode for use in high-frequency surgery, comprising steps of: providing a resonant circuit into which said two electrode parts are incorporated in parallel with one another such that there is a transition impedance between them; measuring a resonant-frequency shift in said resonant circuit; and determining the purely capacitive component of the transition impedance using said resonant-frequency shift.

2. Method according to claim 1, wherein the determination of the purely capacitive component of the transition impedance comprises the following steps:
   providing a basic resonant circuit with a measurement inductance and a coupling capacitance;
   measuring a basic resonant frequency of said basic resonant circuit;
   providing an expanded resonant circuit by incorporating said transition impedance in parallel into said basic resonant circuit;
   measuring a sample resonant frequency of said expanded resonant circuit; and
   determining the capacitive component from the basic resonant frequency, the sample resonant frequency and the measurement inductance, assuming that the transition impedance comprises an ohmic resistance and a capacitive resistance that are parallel to one another in the basic resonant circuit.

3. Method according to claim 2, wherein a measurement of at least one of the basic resonant frequency of the basic resonant circuit and the sample resonant frequency of the expanded resonant circuit comprising steps of: providing a lead to the relevant resonant circuit, applying a measurement alternating voltage to one of the basic resonant circuit and the expanded resonant circuit respectively, measuring the phase angle between current and voltage in a said lead to the relevant resonant circuit, and adjusting the frequency of the measured alternating current until current and voltage are exactly in phase with one another.

4. Method according to claim 3, wherein a square-wave alternating-current signal of constant current amplitude is applied to at least one of said basic resonant circuit and said expanded resonant circuit in order to measure respectively at least one of the basic resonant frequency of the basic resonant circuit and the sample resonant frequency of the expanded resonant circuit.

5. Method according to claim 4, wherein the frequency of said alternating-current signal is adjusted by means of a timer signal in order that the zero crossing and the frequency of said alternating-current signal can be determined by way of the timer signal.

6. Method according to claim 2, wherein a measurement alternating voltage is applied to at least one of said basic resonant circuit and said expanded resonant circuit, the voltage across at least one of said basic resonant circuit and said expanded resonant circuit is measured and the frequency of the measurement alternating voltage is adjusted until the voltage reaches a maximal value in order to measure respectively at least one of the basic resonant frequency of the basic resonant circuit and the sample resonant frequency of the expanded resonant circuit.

7. Method according to claim 2, wherein the ohmic component of the transition impedance is determined by providing a lead to the expanded resonant circuit, measuring the voltage across the expanded resonant circuit and the current in said lead, and deriving the ohmic component of the transition impedance from these measurements.

8. Method according to claim 2, wherein the transition impedance at predetermined time intervals is monitored by measuring the sample resonant frequency of the expanded resonant circuit.

9. Method according to claim 1, wherein during a high-frequency surgical application the current flowing away from each of the electrode parts is measured.

* * * * *